(12) United States Patent
Taeubrich et al.

(10) Patent No.: US 9,592,296 B2
(45) Date of Patent: Mar. 14, 2017

(54) PHARMACEUTICAL COMPOSITION FOR ORAL ADMINISTRATION WITH A STATIN

(75) Inventors: Theresa Taeubrich, Holzkirchen (DE); Patrick Rother, Holzkirchen (DE)

(73) Assignee: HEXAL AG, Holzkirchen (DE)

( * ) Notice: Subject to any disclaimer, the term of this patent is extended or adjusted under 35 U.S.C. 154(b) by 46 days.

(21) Appl. No.: 14/342,439

(22) PCT Filed: Aug. 21, 2012

(86) PCT No.: PCT/EP2012/066288
§ 371 (c)(1),
(2), (4) Date: Mar. 3, 2014

(87) PCT Pub. No.: WO2013/034436
PCT Pub. Date: Mar. 14, 2013

(65) Prior Publication Data
US 2014/0227355 A1  Aug. 14, 2014

(30) Foreign Application Priority Data
Sep. 8, 2011  (EP) .................................... 11180555

(51) Int. Cl.
| *A61K 47/12* | (2006.01) |
| *A61K 9/20* | (2006.01) |
| *A61K 31/366* | (2006.01) |
| *A61K 47/10* | (2006.01) |

(52) U.S. Cl.
CPC ............ *A61K 47/12* (2013.01); *A61K 9/2018* (2013.01); *A61K 9/2054* (2013.01); *A61K 9/2059* (2013.01); *A61K 31/366* (2013.01); *A61K 47/10* (2013.01)

(58) Field of Classification Search
None
See application file for complete search history.

(56) References Cited

U.S. PATENT DOCUMENTS

| 6,096,338 A * | 8/2000 | Lacy et al. ..................... 424/455 |
| 2003/0211151 A1 * | 11/2003 | Tillyer et al. ................. 424/468 |
| 2011/0257240 A1 * | 10/2011 | Pavliv et al. ................. 514/423 |

FOREIGN PATENT DOCUMENTS

| EP | 1992343 A1 | 11/2008 |
| KR | 10-2005-0030282 A | 3/2005 |
| KR | 20050030282 A | 3/2005 |
| WO | WO 2010092450 | * 8/2010 |

OTHER PUBLICATIONS

Rossebø AB, et al. Intensive Lipid Lowering with Simvastatin and Ezetimibe in Aortic Stenosis. NEJM 2008;359(13):1343-56.*
http://blog.fooducate.com/2009/09/10/10-things-to-know-about-propyl-gallate/ (posted Sep. 10, 2009).*
German Office Action for Related Application No. 12758423.3-1455 (Jun. 17, 2016) (5 pages).

* cited by examiner

*Primary Examiner* — David J Blanchard
*Assistant Examiner* — Sarah Chickos
(74) *Attorney, Agent, or Firm* — Lucas & Mercanti, LLP

(57) ABSTRACT

The invention relates to a pharmaceutical composition for oral administration comprising or consisting of (i) 10 to 30% weight, of at least one pharmaceutically active substance selected from the group consisting of water-soluble, oxidatively-degradable statins, preferably atorvastatin, cerivastatin, fluvastatin, lovastatin, pitavastatin, pravastatin, rosuvastatin, simvastatin or a combination thereof, (ii) 0.01 to 3% weight, of a first anti-oxidatively active substance (A1), (iii) 0.01 to 3% weight, of a second anti-oxidatively active substance (A2) that differs from the first anti-oxidatively active substance (A1), and (iv) 60 to 85% weight of at least one additive, selected from the group consisting of filler, binder, flow-regulating agent, disintegrant and anti-blocking agent or a combination thereof, and the use of the pharmaceutical composition in medicine.

17 Claims, 3 Drawing Sheets

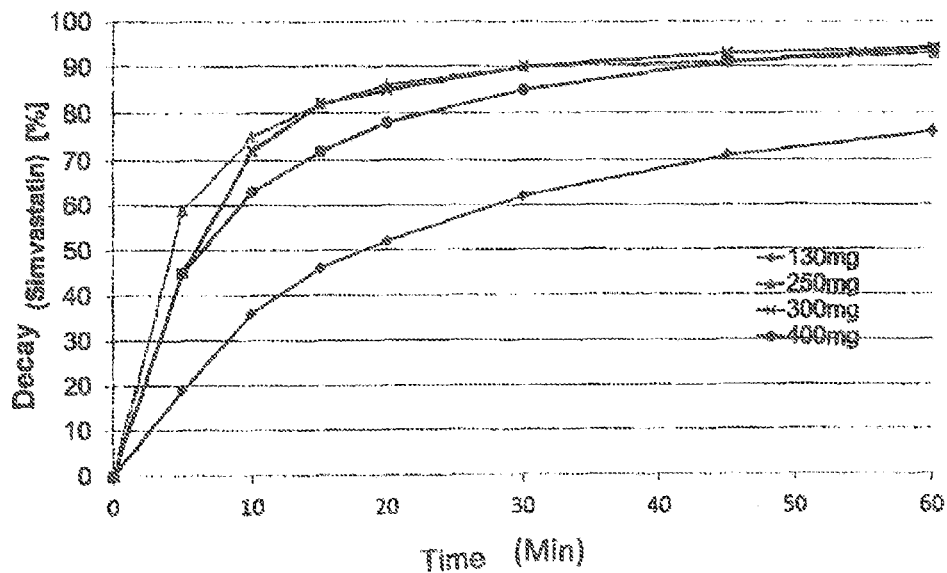
Fig. 1 Decay of simvastatin plot against weight of simvastatin 40 mg film-coated tablets
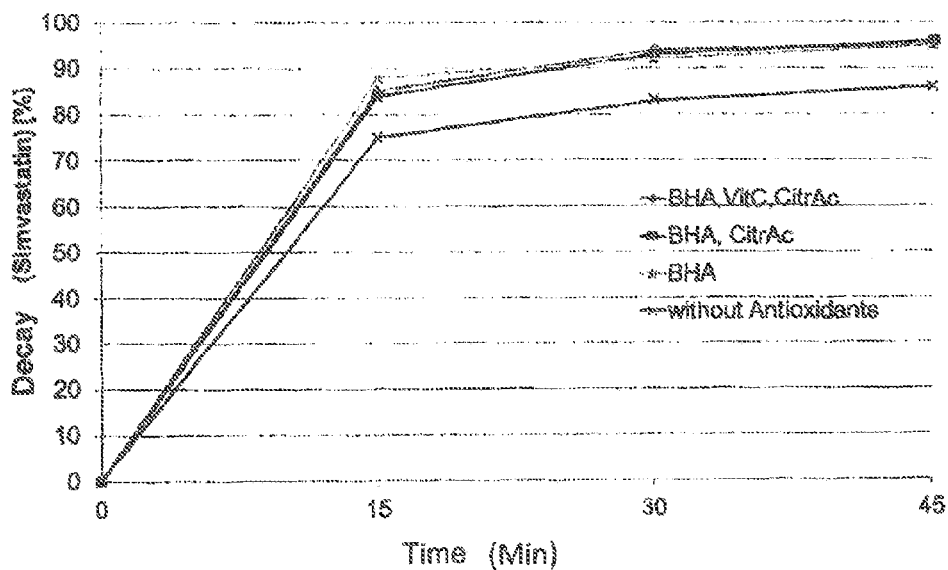
Fig. 2 Decay of simvastatin plot against addition of antioxidant in simvastatin 40 mg film-coated tablets after week 1 at 60°C, 75%RH

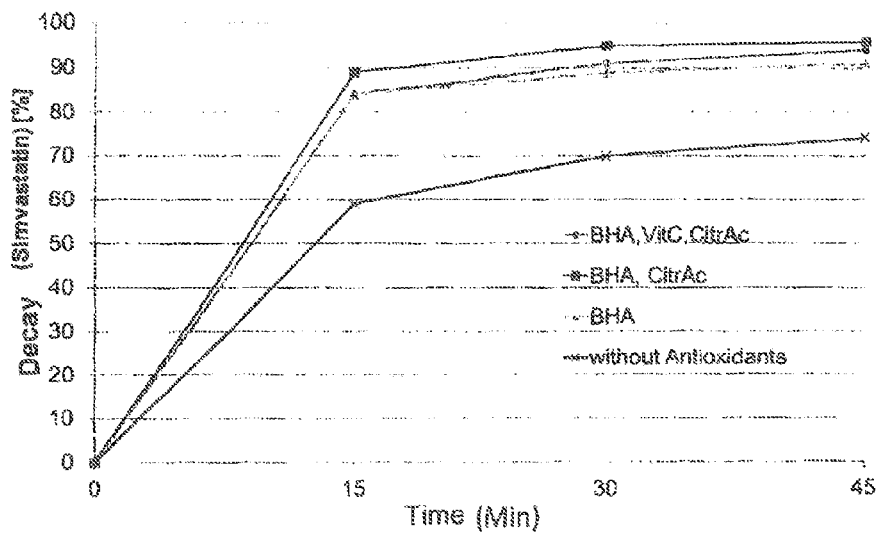
Fig. 3 Decay of simvastatin plot against addition of antioxidant in simvastatin 40 mg film-coated tablets after week 2 at 60°C, 75%RH
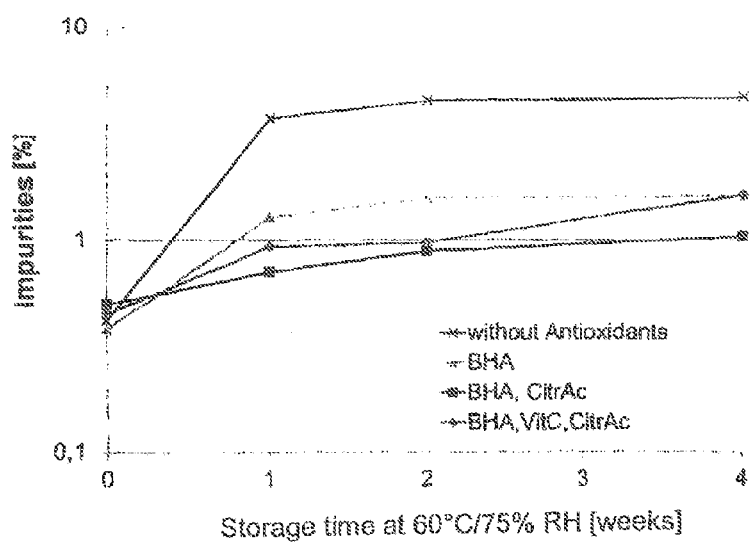
Fig. 4 Impurities plot against addition of antioxidant in simvastatin 40 mg film-coated tablets after storage at 60°C, 75%RH

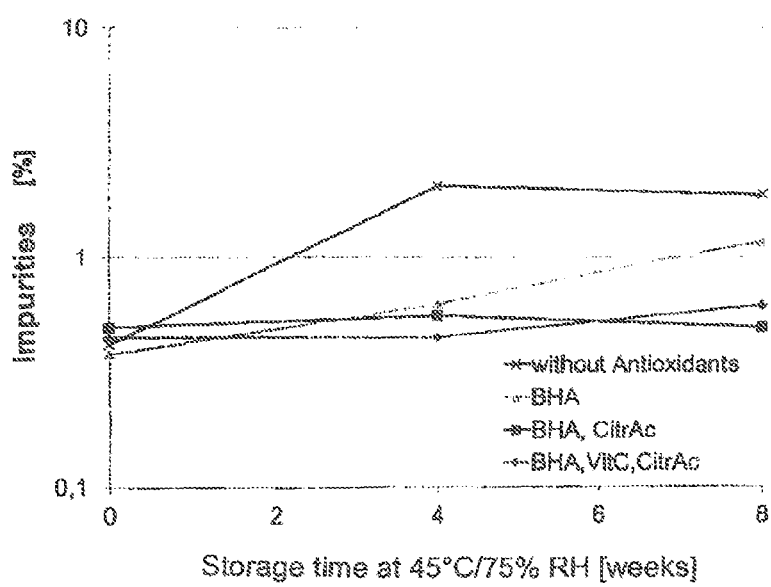
Fig. 5 Impurities plot against addition of antioxidant in simvastatin 40 mg film-coated tablets after storage at 45°C, 75%RH

PHARMACEUTICAL COMPOSITION FOR ORAL ADMINISTRATION WITH A STATIN

CROSS-REFERENCE TO RELATED APPLICATIONS

This application is a 371 of PCT/EP2012/066288, filed Aug. 21, 2012, which claims the benefit of European Patent Application No. 11180555.2, filed Sep. 8, 2011, the contents of each of which are incorporated herein by reference.

FIELD OF THE INVENTION

The invention relates to a pharmaceutical composition for oral administration comprising or consisting of at least one statin, as well as a first and optionally a second anti-oxidatively active substance.

BACKGROUND OF THE INVENTION

Statins as pharmaceutically active substances of biopharmaceutical class II (BCS class II) are considered under pharmaceutical aspects as being unstable and are particularly susceptible to oxidative degradation. To avoid this, different methods respectively proceedings are known. These include the suitable choice of the dosage form, the addition of suitable excipients, as well as the selection of a suitable packaging.

In order to reduce the oxidative degradation rate of statins, they are formulated together with antioxidant substances (antioxidants). By the use of the antioxidants as well as other excipients in the mostly oral pharmaceutical composition the active substance is sufficiently stabilized.

The disadvantage thereof is that for stabilization of the active substance redundant measures are possibly taken.

For example, dosage forms known from the prior art have a quantity of excipient, which due to their amount, have an adverse effect on weight and volume of the dosage form and the production costs. The higher the proportion of excipient, the smaller is also the concentration of the active substance within the formulation. Low concentrations of the active substance also have the effect that the ratio of impurities, such as degradation products of the active substance, in relation to the active substance are disadvantageously increased. Therefore, in general, a high concentration of active substance, i.e. a small ratio of excipients in the formulation is sought.

In case of the statins, as an important aspect it appears that the solubility and the dissolution rate of these active substances increases in the physiological system, the higher the proportion of excipients used in the dosage form is.

As statins in connection with the present invention, pharmaceutically active substances are understood which belong to the pharmacological class of compounds of 3-hydroxy-3-methylglutaryl-coenzyme-A-reductase (HMG-CoA reductase) inhibitors.

Statins are mainly used with lipid disorders as cholesterol-lowering agents and exhibit the highest potency when compared to all medications which affects lipid metabolism.

WO 2004/010 933 A (UNIV LELAND STANFORD JUNIOR [U.S.]; KIM SEUNG [U.S.]; Rulifson INGRID [U.S.]; HORI Yuichi [U.S.]) Jul. 27, 2003 discloses a composition which comprises beside a statin a cholesterol absorption inhibitor, here Ezetimibe, and at least one substance stabilizing the active substance.

It is disadvantageous that the composition only has a relatively low proportion of statin and also the combination of statins and the cholesterol absorption inhibitor Ezetimibe, compared with compositions comprising only statins as a pharmaceutically effective ingredient, shows a higher number of serious side effects and thus poorer patient compliance.

KR 20050030282 A (KOREA UNITED PHARM INC) Sep. 25, 2003 discloses a dosage form comprising simvastatin dissolved in a soft capsule.

Adversely in this case turns out to be the high proportion of surface-active substances, which is necessary to control the bioavailability of the statin.

The statins usable in connection with the compositions described in connection with the present invention are defined by their biopharmaceutical class. The biopharmaceutical classification system (BCS) classifies pharmaceutically effective substances in terms of their bioavailability to be expected.

The statins used in the compositions of this invention are classified in the biopharmaceutical class II and have a low solubility at high membrane permeability. The resorption is controlled by the solubility and/or the solution rate of the drugs.

SUMMARY OF THE INVENTION

It was an objective of the present invention to overcome the disadvantages of known pharmaceutical compositions and to provide a pharmaceutical composition in which one or more statins are present in pharmaceutically acceptable stability and bioavailability/solubility and which at a high content of pharmaceutically effective substance having a low weight respectively volume may be produced inexpensive and preferred as a solid pharmaceutical dosage form. It was in particular an objective of the invention to provide a pharmaceutical composition comprising at least one statin, in which the type and portion of excipients and the drug-excipient ratio is optimized compared to known formulations.

DETAILED DESCRIPTION OF THE INVENTION

These objectives are solved by providing a pharmaceutical composition for oral administration comprising or consisting of at least one pharmaceutically active substance selected from the group consisting of water-soluble, oxidatively-degradable statins, preferably atorvastatin, cerivastatin, fluvastatin, lovastatin, pitavastatin, pravastatin, rosuvastatin, simvastatin, or combinations thereof, and a first anti-oxidatively active substance (A1) and a second anti-oxidatively active substance (A2) different from the first anti-oxidatively active substance (A1). According to the invention it is provided that the pharmaceutically composition based on their total weight has 10 to 30% by weight of the at least one pharmaceutically active substance, 0.01 to 3% by weight of the first anti-oxidatively active substance (A1) and 0.01 to 3% by weight of the second anti-oxidatively active substance (A2). The composition further comprises between 60 and 85% by weight of at least one additive selected from the group consisting of filler, binder, flow regulating agent, disintegrant, and anti-blocking agent or a combination thereof. Preferably 0 to 3% by weight of the composition are provided by a film coating.

It was determined that by using only one anti-oxidatively active substance with a low amount of 0.01 to 3% by weight in the formulation a significant increase in drug stability, compared to a formulation containing no anti-oxidatively substances can already be achieved.

Surprisingly it was found that the achieved drug stability, in comparison to those known from prior art formulations, in which the active ingredient is conventionally stabilized by using two or more anti-oxidatively substances in some extend in higher proportions, is partially enhanced, but at least equal.

Due to a reduced amount of excipients used or a complete abandonment of unnecessary excipients, the pharmaceutical composition of the invention has, when compared to known compositions, an optimized active substance:excipient ratio or active substance:antioxidant ratio such that the active substance is provide sufficiently stabilised in a high amount relative to the overall weight of the composition and has at the same time a pharmaceutically acceptable dissolution rate.

By adding a second anti-oxidatively active substance (A2) differin from the first anti-oxidatively active substance (A1), the affinity of disintegration of the at least one pharmaceutically active substance of BCS class II can be further reduced. However, the proportion of the second anti-oxidatively active substance (A2) can be kept very low.

By complete or partial abandonment of redundant measures a reduction of the production costs for the inventive composition can be guaranteed when compared to known compositions with comparable drug stability. The inventive composition and a dosage form formed therefrom is characterized in comparison with the compositions known from the prior art by an increased proportion of a pharmaceutically active substance. Through to overall reduced size of the dosage form and the reduced number of necessary medication doses, patient compliance is increased. Because of the increased proportion of statin in the composition it can be abstained from a combined active substance and thus the number of possible side effects be reduced.

In addition to reduce side effects, by avoiding unnecessary and/or unnecessarily high levels of pharmaceutical excipients the total weight of the preferred solid pharmaceutical composition may be reduced, and thus the possible percentage of the active ingredient in the pharmaceutical composition be increased. Because of the reduced weight a reduction of the size or the volume of the dosage form can be achieved. This on the other hand increases patient compliance. Particularly it is advantageous if the content of the statin in the pharmaceutical composition amounts from 11 to 25% by weight, preferably from 12.5 to 20% by weight.

It is considered to be advantageous if the ratio of the first anti-oxidatively active substance (A1) in the pharmaceutical composition amounts from 0.01 to 2.5% by weight, preferably 0.01 to 1% by weight, more preferably 0.01 to 0.1% by weight, more preferably 0.01 to 0.05% by weight. The aforementioned percent by weight ranges have surprisingly shown that the positive effects in the production and use of the pharmaceutical composition described above can be obtained and an anti-oxidatively active substance (A1) used in the specified weight percentage at the same time ensures the stability of the pharmaceutically active substance, which corresponds to or even exceeds that of known compositions.

A preferred embodiment of the invention provides that a second anti-oxidatively active substance (A2), different from the first anti-oxidatively active substance (A1), is used in the pharmaceutical composition. The content thereof is favorably from between 0.01 to 2.5% by weight, preferably 0.1 to 2% by weight, more preferably 0.5 to 2% by weight, in particular preferably 1 to 2% by weight, relative to the total weight of the pharmaceutical composition. The use of a second anti-oxidatively active substance has an effect on the decay rate of the pharmaceutically active substance. The addition of another anti-oxidatively active substance (A2) further improves the durability and stability of the pharmaceutically active substance, without adversely affecting the drug dissolution rate.

In particular, pharmaceutically active substances of biopharmaceutical class II are susceptible to oxidative degradation.

According to the invention, the pharmaceutically active substance is selected from the group consisting of water-unsoluble, oxidatively degradable statins and in this case preferably from atorvastatin, cerivastatin, fluvastatin, lovastatin, pitavastatin, pravastatin, rosuvastatin, simvastatin, or combinations thereof.

The pharmaceutical composition according to the present invention surprisingly showed that the oxidative degradation of the named statins or combinations thereof in the inventive pharmaceutical composition can be significantly reduced already, if the pharmaceutically active substance is formulated with a first antioxidant substance in the proportions previously described, without using a second antioxidant substance. However, the addiction to degrade is further reduced and kept to a minimum by the adding a second antioxidant substance which is different from the first one. By combining of at least two anti-oxidatively active substances their absolute amount in the composition can be reduced. It has been shown to be particularly advantageous if the pharmaceutically active substance is simvastatin. In this case by abandonment of a redundant antioxidant measure the total weight of the pharmaceutical composition is reduced and the relative proportion of a pharmaceutically active substance in the overall composition increased. Simultaneously, because of reduced weight and the abandonment of additional antioxidant measures, the costs of the pharmaceutical composition are essential lowered and compliance is increased. Solubility and stability of simvastatin in the inventive formulation correspond to or even exceed those of known simvastatin formulations.

As anti-oxidatively substances in the context of the present invention considered are chain terminators, reducing agents, free radical scavengers and chelating agents. Such anti-oxidatively substances are classified according to their type of activity in the four categories mentioned above. It is considered advantageously in the context of the present invention if the first anti-oxidatively active substance (A1) is selected from chain terminators, reducing agents, free radical scavengers or chelating agents. It is considered to be particularly advantageous when the first anti-oxidatively active substance (A1) is at least one chain terminator from the group of phenols and phenol ethers, especially butylated hydroxyanisole (BHA).

According to the invention it is provided that, if necessary, a second anti-oxidatively active substance (A2) is used in the pharmaceutical composition, wherein the second anti-oxidatively active substance (A2) differs from the first anti-oxidatively active substance (A1). Is considered favorable in this context when the second anti-oxidatively active substance (A2) is a reducing agent.

Preferably, the second anti-oxidatively active substance (A2) is an organic acid, in particular citric acid or ascorbic acid, citric acid is particularly preferred. Furthermore, the second anti-oxidatively active substance (A2) can be a combination of two to four, preferably two organic acids, in particular a combination of citric acid and ascorbic acid. This results in a pharmaceutical composition, in which besides the pharmaceutically active substance a first anti-oxidatively active substance, for example the chain terminator butylated hydroxyanisole and a second anti oxidatively active substance, for example the reducing agent citric acid are used.

The combination of a first and a second anti-oxidatively active substance with at least one active ingredient as described above, surprisingly causes a further reduction of the addiction to degrade respectively a decline in the dissolution of the pharmaceutically active substance(es) in the composition and allows relative to a higher proportion of active substance in particular the reduction of the proportion of butylated hydroxyanisole in the composition.

A pharmaceutical composition according to the present invention preferably for oral administration preferably comprises or consists of (i) 10 to 30% by weight, in particular 11 to 20% by weight of at least one statin, in particular atorvastatin, cerivastatin, fluvastatin, lovastatin, pitavastatin, pravastatin, rosuvastatin, simvastatin or combinations thereof, preferably simvastatin, (ii) 0.01 to 0.1% by weight, in particular 0.01 to 0.04% by weight, preferably 0.01 to 0.03% by weight of a first anti-oxidatively active substance (A1), preferably butylated hydroxyanisole, and (iii) 0.01 to 3% by weight, in particular 0.5 to 2.5% by weight, preferably 0.8 to 1.8% by weight, in particular preferred 0.9 to 1.7% by weight of a second anti-oxidatively active substance (A2), preferably citric acid and/or ascorbic acid. Particularly preferred is citric acid as a second anti-oxidatively active substance. The details of the weight percentages relate to the total weight of the pharmaceutical composition.

The inventive pharmaceutical composition comprises in case of a solid oral formulation further (iv) at least one excipient or additive from the group consisting of filler, binder, flow-regulating agent, disintegrant and anti-blocking agents. Of course, there is the possibility that the aforementioned excipients or additives are used in combination in the pharmaceutical composition.

An advantageous embodiment of the pharmaceutical composition provides that this is present as a compressed tablet. In order to further alleviate the ingestion of the tablet it has in particular a surface coating (film coated tablet).

An advantageous embodiment of the pharmaceutical composition provides that the composition is available as a film-coated tablet, or as immediate release tablet.

Alternatively to the pressing operation as a tablet there is the possibility that the composition is filled into a gelatin hard capsule.

The invention also includes the use of the pharmaceutical composition as described above in medicine.

The pharmaceutical composition according to the invention is in particular suitable as a HMG-CoA reductase inhibitor, use for the treatment of fat metabolism disorders is preferred.

Subsequently the invention is illustrated by examples. The shown embodiments are intended only to illustrate the invention, the same is not limited to the embodiments shown in the embodiments.

EXAMPLE 1

Preparation of the Pharmaceutical Composition for Oral Administration According to the Present Invention A wet granulation of pharmaceutically active substance, microcrystalline cellulose, starch, and lactose monohydrate is performed. As first anti-oxidatively active substance butylated hydroxyanisole is used, which is dissolved in ethanol. The antioxidative acid used is dissolved in water. A standard fluidized drier is used, to achieve a loss on drying of 2 to 2.5% of the dried granules. The dried granules are mixed with magnesium stearate and the final mixture is performed in a drum mixer (bin blender). Tableting is done in a standard rotary press with conventional biconvex press punches (diameter 7 to 11 mm, depending on the tablet weight) with simple breakline with shallow radii. The formed tablets are suitable for film coating.

A HPMC (hydroxypropyl methylcellulose) based coating suspension is prepared.

The amount of lacquer dry substance that is necessary to cover the tablet core, is determined empirically.

The tablets prepared in the above-mentioned method have compositions with the given weight proportions as specified in the following Tables 1 to 5 (Tab. 1 to Tab. 3). There are produced tablets with a tablet weight of the coated tablet of between 200 and 350 mg.

The proportion of pharmaceutically active substance is indicated in the example tablets at 40 mg. The inventive composition and the dosage forms formed thereof are thus smaller, based on the total weight, with an increased active substance content and can thus be swallowed easier than prior art formulations having the same amount of active substance. Simvastatin is used as pharmaceutically active substance in all embodiments.

TABLE 1

| Components of the tablet | Weight % of the coated tablet |
| --- | --- |
| Simvastatin | 11.4 |
| Starch | 14.0 |
| Lactose monohydrate | 63.6 |
| Microcrystalline cellulose | 7.0 |
| Magnesium stearate | 0.6 |
| Butylhydroxyanisol | 0.01 |
| Citric acid | 0.9 |
| Film coating | 2.5 |
| Total weight of the coated tablet | 350 mg |

TABLE 2

| Components of the tablet | Weight % of the coated tablet |
| --- | --- |
| Simvastatin | 13.3 |
| Starch | 13.3 |
| Lactose monohydrate | 61.7 |
| Microcrystalline cellulose | 6.7 |
| Magnesium stearate | 0.7 |
| Butylhydroxyanisol | 0.03 |
| Citric acid | 1.7 |
| Film coating | 2.6 |
| Total weight of the coated tablet | 300 mg |

TABLE 3

| Components of the tablet | Weight % of the coated tablet |
| --- | --- |
| Simvastatin | 16.0 |
| Starch | 16.0 |
| Lactose monohydrate | 47.9 |
| Microcrystalline cellulose | 16.0 |
| Magnesium stearate | 0.8 |
| Butylhydroxyanisol | 0.03 |
| Citric acid | 1.0 |
| Film coating | 2.3 |
| Total weight of the coated tablet | 250 mg |

TABLE 4

| Components of the tablet | Weight % of the coated tablet |
| --- | --- |
| Simvastatin | 20.0 |
| Starch | 20.0 |
| Lactose monohydrate | 30.7 |
| Microcrystalline cellulose | 25.0 |
| Magnesium stearate | 0.9 |
| Butylhydroxyanisol | 0.04 |
| Citric acid | 1.4 |
| Film coating | 2.0 |
| Total weight of the coated tablet | 200 mg |

EXAMPLE 2

Analytical Methods/Stability Testing

Dissolution tests were carried out using Na-Phosphate/SDS-Puffer pH 7.0 and analyzed by HPLC using UV detection. Impurities were analyzed by HPLC using gradient elution and using a $NaH_2PO_4$ buffer pH 4.5/acetonitrile. The tablets were stored for 4 weeks at 25° C./60% RH, 45° C./75% RH and in addition at 60° C./75% RH.

FIG. 1 shows the relation between tablet weight and dissolution of the pharmaceutically active substance.

FIG. 2 shows the results after 1 week of storage at a temperature of 60° C. and 75% relative humidity (RH).

FIG. 3 shows that the curves from the $2^{nd}$ week of storage become more clearly distinguishable.

FIG. 4 shows an analysis of the impurities. Small differences in the dissolution data can be investigated more accurately by this impurity analysis.

FIG. 5 illustrates the analysis of the impurities and confirms the values shown above in FIG. 4.

The values were determined in a standardized accelerated stability testing (ASII, 45° C./75% RH).

Key to the Figures:
BHA: butylated hydroxyanisole
VitC: Vitamin C (ascorbic acid)
CitrAc: citric acid
without antioxidants: without antioxidants It can be gathered from the figures that pharmaceutical compositions according to the invention as defined above, have compared with conventional compositions comparable or improved stability values. Surprisingly it was found that the lowest limit for the weight of the tablets containing 40 mg of simvastatin as an ingredient, preferably were between 250 mg and 130 mg tablets basic weight. The active substance in this case exhibits both highest stability and sufficient dissolution rate.

The invention includes the following items:
A pharmaceutical composition for oral administration comprising or consisting of:
(i) 10 to 30% by weight of at least one statin;
(ii) 0.01 to 3% by weight of a first anti-oxidatively active substance (A1),
(iii) 0.01 to 3% by weight of a second anti-oxidatively active substance (A2), different from the first anti-oxidatively active substance (A1), and
(iv) 60 to 85% by weight of at least one additive selected from the group consisting of filler, binder, flow regulating agent, disintegrant, and anti-blocking agent or a combinations thereof.

A pharmaceutical composition as described above, wherein the proportion of at least one pharmaceutically active substance in the pharmaceutical composition amounts from 11 to 25% by weight, preferably from 12.5 to 20% by weight.

A pharmaceutical composition as described above, wherein the proportion of the first anti-oxidatively active substance (A1) in the pharmaceutical composition is 0.01 to 2.5% by weight, preferably 0.01 to 1% by weight, 0.01 to 0.1% by weight, or 0.01 to 0.05% by weight.

A pharmaceutical composition as described above, wherein the ratio of the second antioxidant agent (A2) in the pharmaceutical composition is 0.01 to 2.5% by weight, preferably 0.1 to 2% by weight, 0.5 to 2 by weight % or 1 to 2 by weight.

A pharmaceutical composition as described above, wherein the proportion of the second anti-oxidatively active substance (A2) in the pharmaceutical composition is 0.01 to 2.5% by weight, preferably 0.1 to 2% by weight, 0.5 to 2% by weight or 1 to 2% by weight.

A pharmaceutical composition as described above, wherein the pharmaceutically active substance is selected from the group consisting of water-insoluble, oxidatively degradable statin, preferably atorvastatin, cerivastatin, fluvastatin, lovastatin, pitavastatin, pravastatin, rosuvastatin, simvastatin, or combinations thereof.

A pharmaceutical composition as described above, wherein the pharmaceutically active substance is simvastatin.

A pharmaceutical composition as described above, wherein the first anti-oxidatively active substance (A1) is selected from chain terminators, reducing agents, radical scavengers and chelants.

A pharmaceutical composition as described above, wherein the first anti-oxidatively active substance (A1) is at least one chain terminator selected from the group of phenols and phenol ethers, in particular butylhydroxyanisole.

A pharmaceutical composition as described above, wherein the second anti-oxidatively active substance (A2) is a reducing agent.

A pharmaceutical composition as described above, wherein the second anti-oxidatively active substance (A2) is an organic acid, in particular citric acid or ascorbic acid or a combination of two to four, preferably two organic acids, in particular a combination of citric acid and ascorbic acid.

A pharmaceutical composition for oral administration comprising or consisting of:
(i) 10 to 30% by weight, in particular 11 to 20% by weight of at least one statin, especially atorvastatin, cerivastatin, fluvastatin, lovastatin, pitavastatin, pravastatin, rosuvastatin, preferably simvastatin,
(ii) 0.01 to 0.1% by weight, in particular 0.01 to 0.04% by weight, preferably 0.01 to 0.03% by weight of a first anti-oxidatively active substance (A1), as defined above, preferably butylated hydroxyanisole, and
(iii) 0.01 to 3% by weight, in particular 0.5 to 2.5% by weight, preferably 0.8 to 1.8% by weight, particularly preferred 0.9 to 1.7% by weight of a second anti-oxidatively active substance (A2), as defined above, preferably citric acid or ascorbic acid.

A pharmaceutical composition as described above wherein the at least one additive is selected from the group consisting of filler, binder, flow-regulating agent, disintegrant, anti-blocking agent or combinations thereof.

A pharmaceutical composition as described above, wherein the composition is pressed in tablet form, in particular wherein said tablet has a surface coating.

A pharmaceutical composition as described above, wherein the composition is present as a film-coated tablet.

A pharmaceutical composition as described above, wherein the composition is present as an immediate release tablet.

A pharmaceutical composition as described above, wherein 0 to 3% by weight of the composition are formed by a film coating.

A pharmaceutical composition as described above, wherein the composition is filled into a gelatin hard capsule.

The use of the pharmaceutical composition as described above, in medicine, in particular as a HMG-CoA reductase inhibitor, preferably for the treatment of lipid metabolism disorders.

The invention claimed is:

1. Pharmaceutical composition for oral administration consisting of:
   (i) 10 to 30% by weight of simvastatin,
   (ii) 0.01 to 3% by weight of a first anti-oxidatively active substance (A1) being butylated hydroxyanisole,
   (iii) 0.01 to 3% by weight of a second anti-oxidatively active substance (A2), different from the first anti-oxidatively active substance (A1), being citric acid, and
   (iv) 60 to 85% by weight of at least one additive selected from the group consisting of fillers, binders, flow regulating agents, disintegrants, anti-blocking agents, lubricants and combinations thereof,
   wherein the composition has a weight between 130 milligrams and 300 milligrams up to 300 mg: and
   wherein the composition is present as a film-coated tablet.

2. Pharmaceutical composition according to claim 1, wherein the percent of the statin in the pharmaceutical composition amounts from 11 to 25% by weight.

3. Pharmaceutical composition according to claim 1, wherein the percent of the first anti-oxidatively active substance (A1) in the pharmaceutical composition amounts from 0.01 to 2.5% by weight.

4. Pharmaceutical composition according to claim 1, wherein the percent of the second anti-oxidatively active substance (A2) in the pharmaceutical composition amounts from 0.01 to 2.5% by weight.

5. Pharmaceutical composition for oral administration consisting of:
   (i) 10 to 30% by weight of simvastatin,
   (ii) 0.01 to 0.1% by weight of the first anti-oxidatively active, substance (A1) as butylated hydroxyanisole, and
   (iii) 0.01 to 3% by weight of the second anti-oxidatively active substance (A2) as citric acid, and
   (iv) at least one additive selected from the group consisting of fillers, binders, flow regulating agents, disintegrants, anti-blocking agents, lubricants and combinations thereof,
   wherein the composition has a weight between 130 milligrams and 300 milligrams, and
   wherein the composition is present as a film-coated tablet.

6. Pharmaceutical composition according to claim 5, wherein the quantitative ratio of A1 to A2 amounts from 1:95 to 1:30.

7. Pharmaceutical composition according to claim 1, wherein the additive is provided as starch, lactose monohydrate, microcrystalline cellulose, or magnesium stearate.

8. Pharmaceutical composition according to claim 1, wherein 0 to 3% by weight of the composition is formed by a film coating.

9. Pharmaceutical composition according to claim 1, wherein the composition is present as an immediate release tablet.

10. Method for the treatment of lipid metabolism disorders comprising orally administering a composition of claim 1 to a patient in need thereof.

11. Pharmaceutical composition according to claim 2, wherein the proportion of the statin in the pharmaceutical composition amounts from 12.5 to 20% by weight.

12. Pharmaceutical composition according to claim 3, wherein the percent of the first anti-oxidatively active substance (A1) in the pharmaceutical composition amounts from 0.01 to 1% by weight.

13. Pharmaceutical composition according to claim 12, wherein the percent of the first anti-oxidatively active substance (A1) in the pharmaceutical composition amounts from 0.01 to 0.05% by weight.

14. Pharmaceutical composition according to claim 4, wherein the percent of the second anti-oxidatively active substance (A2) in the pharmaceutical composition amounts from 0.01 to 1% by weight.

15. Pharmaceutical composition according to claim 14, wherein the percent of the second anti-oxidatively active substance (A2) in the pharmaceutical composition amounts from 0.01 and 0.05% by weight.

16. Pharmaceutical composition according to claim 6, wherein the quantitative ratio of A1 to A2 amounts from 1:90 to 1:36.

17. Pharmaceutical composition according to claim 1, wherein said tablet has a weight between 130 milligrams and 250 milligrams.

* * * * *